(12) United States Patent
Lee et al.

(10) Patent No.: US 11,517,441 B2
(45) Date of Patent: Dec. 6, 2022

(54) ACETABULAR APPARATUS WITH DUAL MOBILITY FOR HIP REVISION SURGERY

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Stephen J. Lee, Memphis, TN (US); Jeffrey J. Shea, Memphis, TN (US); David W. Rister, Nesbit, MS (US)

(73) Assignees: Smith & Nephew, Inc., Memphis, TN (US); Smith & Nephew Asia Pacific Pte. Limited, Singapore (SG); Smith & Nephew Orthopaedics AG, Zug (CH)

(*) Notice: Subject to any disclaimer, the term of this patent is extended or adjusted under 35 U.S.C. 154(b) by 141 days.

(21) Appl. No.: 17/015,249

(22) Filed: Sep. 9, 2020

(65) Prior Publication Data

US 2021/0077262 A1 Mar. 18, 2021

Related U.S. Application Data

(60) Provisional application No. 62/899,913, filed on Sep. 13, 2019.

(51) Int. Cl.
*A61F 2/34* (2006.01)
*A61F 2/36* (2006.01)
*A61F 2/46* (2006.01)

(52) U.S. Cl.
CPC .............. *A61F 2/34* (2013.01); *A61F 2/3609* (2013.01); *A61F 2/4609* (2013.01); *A61F 2002/3435* (2013.01)

(58) Field of Classification Search
CPC ...... A61F 2/32; A61F 2/34; A61F 2002/3208; A61F 2002/3216
See application file for complete search history.

(56) References Cited

U.S. PATENT DOCUMENTS

| 5,425,778 A | * | 6/1995 | Zichner | ............... A61F 2/34 623/22.29 |
| 2005/0288793 A1 | * | 12/2005 | Dong | ............... A61F 2/34 623/22.32 |
| 2012/0016486 A1 | * | 1/2012 | Yokoo | ............... A61F 2/4609 623/22.24 |

(Continued)

OTHER PUBLICATIONS

"R3 Acetabular System—Poly", Smith & Nephew, Inc., www.smith-nephew.com, copyright 2010.

(Continued)

*Primary Examiner* — Brian A Dukert
(74) *Attorney, Agent, or Firm* — KDB Firm PLLC

(57) ABSTRACT

Prostheses, acetabular apparatuses, and methods of use are disclosed. In some embodiments, an acetabular apparatus includes an acetabular cup, a pre-assembled liner and flange construct, and a dual mobility bearing (e.g., a dual articulating femoral head component and insert). In one embodiment, the pre-assembled liner and flange construct may be coupled together by a band coupled to the flanges, the band being arranged and configured to be pressed onto an outer surface of a liner. The pre-assembled liner and flange construct being arranged and configured to accept the dual mobility bearing so that it is freely rotatable relative thereto during use.

20 Claims, 11 Drawing Sheets

(56) References Cited

U.S. PATENT DOCUMENTS

2015/0025647 A1\* 1/2015 Zhang ................ A61F 2/32
623/22.18

OTHER PUBLICATIONS

"R3 Acetabular System—Constrained Liner", Smith & Nephew, Inc., www.smith-nephew.com, copyright 2010.
"Zimmer Trabecular Metal Acetabular Revision System", Zimmer, Inc., www.zimmer.com, copyright 2015.
"Max-Ti Modular Protrusio Cage", Biomet Orthopedics, Inc., www.biomet.com, copyright 2006.

\* cited by examiner

ACETABULAR APPARATUS WITH DUAL MOBILITY FOR HIP REVISION SURGERY

CROSS-REFERENCE TO RELATED APPLICATIONS

This is a non-provisional of, and claims the benefit of the filing date of, U.S. provisional patent application No. 62/899,913, filed Sep. 13, 2019, entitled "Acetabular Apparatuses for Hip Revision Surgery" the entirety of which application is incorporated by reference herein.

FIELD OF THE DISCLOSURE

The present disclosure relates generally to orthopedic apparatuses and methods to address acetabular defects, and particularly to a dual mobility acetabular implant incorporating a dual mobility bearing (e.g., a dual articulating femoral head component and insert) along with a pre-assembled liner and flange construct.

BACKGROUND OF THE DISCLOSURE

Articulating regions of the anatomy can include areas where two bone sections move relative to one another. For example, an acetabulum can provide a region for articulation with a femoral head. The articulating region, however, can become injured or worn, and thus require replacement with one or more implants. Such implants can replace the acetabulum, the femoral head, and various other portions of the femur, or other combinations thereof. The replacement of both the acetabulum and the femoral head is generally referred to as a total joint replacement.

Acetabular implants, apparatuses, prostheses, or devices (used interchangeably herein without the intent to limit) are one type of implants currently used to address acetabular defects in which large portions of a patient's medial wall are missing. Referring to FIG. 1, one method for addressing acetabular defects involves implanting an acetabular implant 100 into a patient's acetabular region. Generally speaking, this involves implanting an acetabular cup or shell 110 (used interchangeably herein without the intent to limit) into the patient's acetabular region. The acetabular cup 110 may be secured to the patient's acetabulum via, for example, fasteners, adhesive, cement, etc. Next, an acetabular cage 130 may be inserted inside of the cup 110. In use, the acetabular cage 130 may be coupled to the acetabular cup 110 via, for example, fasteners, adhesive, cement, etc. The acetabular cage 130 generally includes a central section arranged and configured to be received within the cup 110, and superior and inferior flanges 132, 134 extending from the central section. In use, the superior and inferior flanges 132, 134 may be bent, manipulated, etc. by a surgeon in a manner that somewhat matches the patient's bone (e.g., patient's iliac and ischial anatomy). The flanges 132, 134 are arranged and configured to receive screws for coupling the flanges 132, 134, and hence the acetabular implant 100, to host bone. Finally, a liner 150 is implanted into the cage 130. In use, the liner 150 may be coupled to the cage 130 via, for example, an adhesive, cement, etc. Thus, the liner 150 may be inhibited from moving, articulating, or the like, relative to the cage 130. In use, the liner 150 receives the femoral head 170 of, for example, a hip implant 175. In use, the femoral head 170 is arranged and configured to articulate relative to the liner 150.

Conventional acetabular implants such as, for example, the acetabular implant 100 shown in FIG. 1, suffer from limited sizing of, for example, the femoral head (e.g., femoral head 170), because of the added interior thickness caused by positioning the cage 130 within the cup 110, as well as the necessary thickness of placing the liner 150 within the cage 130. As a result, in order to minimize the overall size of the implant 100, the size of the femoral head 170 needs to be minimized.

More recently, referring to FIG. 2, dual mobility acetabular implants 200 have been developed. Dual mobility acetabular implants 200 have shown promise in reducing the rate of dislocation by introducing increased femoral head sizes as compared to conventional acetabular apparatuses such as, for example, acetabular implant 100 shown in FIG. 1. Generally speaking, as shown, current dual mobility acetabular implants 200 include an acetabular cup 210 for implanting into a patient's acetabular region, a liner 220 arranged and configured to be inserted inside of the cup 210, an insert 240 arranged and configured to be inserted inside of the liner 220, and a femoral head 270 of, for example, a hip implant 275. In use, the insert 240 is arranged and configured to articulate relative to the liner 220 and the femoral head 270 is arranged and configured to articulate relative to the insert 240. Thus arranged, dual mobility acetabular implants utilize two points of articulation to provide increased range of motion. That is, dual mobility acetabular devices enable articulation between the femoral head 270 and the insert 240, and between the insert 240 and the liner 220.

However, conventional dual mobility acetabular implants such as, dual mobility acetabular implant 200 shown in FIG. 2, do not incorporate flanges for coupling to the host bone.

Thus, it would be beneficial to provide a dual mobility acetabular implant that combines dual mobility with a cup-cage system to provide increased range of motion and prevent dislocations as provided by dual mobility acetabular implants, while enabling a surgeon to utilize flanges for coupling the acetabular implant to the host bone.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a dual mobility acetabular implant arranged and configured to be implanted into a patient's bone (e.g., a patient's acetabulum). The dual mobility acetabular implant including an acetabular cup having a curved outer surface arranged and configured to contact a patient's bone (e.g., a patient's acetabulum) and an interior cavity having an interior curved surface; a pre-assembled liner and flange construct, the pre-assembled liner and flange construct being arranged and configured to be at least partially received within the interior cavity of the acetabular cup, the pre-assembled liner and flange construct including a liner having a curved outer surface arranged and configured to contact the interior curved surface of the acetabular cup and an interior cavity having an interior curved surface, the pre-assembled liner and flange construct further includes one or more flanges arranged and configured to contact host bone; and a dual articulating bearing including an insert and a femoral component, the insert having a curved outer surface arranged and configured to contact and articulate relative to the interior curved surface of the liner and an interior curved surface arranged and configured to contact and articulate relative to an outer curved surface of the femoral head component.

In one embodiment, the pre-assembled liner and flange construct includes a flange device including a body portion coupled to the liner and one or more flanges extending from the body portion, the one or more flanges arranged and configured to contact host bone.

In one embodiment, the body portion of the flange device is arranged and configured to be press-fitted onto the curved outer surface of the liner.

In one embodiment, the flange device includes a body portion and first and second flanges, the flange device being integrally formed.

In one embodiment, an exterior surface portion of the curved outer surface of the liner includes a tapered profile for receiving the body portion of the flange device.

In one embodiment, the flange device including the body portion and the one or more flanges is monolithic (e.g., integrally formed).

In one embodiment, the pre-assembled liner and flange construct including the flange device and the liner is monolithic (e.g., integrally formed).

In one embodiment, the flange device is manufactured from a metal, the liner is manufactured from a ceramic or a metal, the metal being ceramicised or non-ceramicised.

In one embodiment, the acetabular cup includes one or more openings arranged and configured to receive one or more fasteners, respectively, for coupling the acetabular cup to the patient's acetabulum.

In one embodiment, the pre-assembled liner and flange construct is coupled to the acetabular cup so that relative movement therebetween is inhibited.

In one embodiment, the one or more flanges are contourable to match the host bone.

In one embodiment, the one or more flanges include a plurality of openings for receiving fasteners for coupling the one or more flanges to the host bone.

In one embodiment, a rotational center point of the liner is offset (e.g., lateralized, medialized, or eccentric) relative to a center point of the acetabular cup.

In one embodiment, an exterior surface of the liner include a different angle, a different curvature, or a combination thereof, relative to an interior surface of the acetabular cup so that the liner can be adjusted relative to the acetabular cup. For example, to adjust the version.

The present disclosure also provides a pre-assembled liner and flange construct for use in a dual mobility acetabular implant, the pre-assembled liner and flange construct including a liner having a curved outer surface arranged and configured to contact an interior curved surface of an acetabular cup, and an interior cavity having an interior curved surface arranged and configured to contact a curved outer surface of a dual articulating bearing so that the bearing can articulate relative to the pre-assembled liner and flange construct; and one or more flanges for contacting host bone.

In one embodiment, the pre-assembled liner and flange construct includes a flange device including a body portion arranged and configured to engage the liner, and the one or more flanges extending from the body portion, the one or more flanges arranged and configured to contact host bone.

In one embodiment, the body portion of the flange device is arranged and configured to be press-fitted onto the curved outer surface of the liner.

In one embodiment, the flange device including the body portion and the one or more flanges are integrally formed.

In one embodiment, an exterior surface portion of the curved outer surface of the liner includes a tapered profile for receiving the body portion of the flange device.

In one embodiment, the pre-assembled liner and flange construct is monolithic.

In one embodiment, the flange device is manufactured from a metal, the liner is manufactured from a ceramic or a metal, the metal being ceramicised or non-ceramicised.

In one embodiment, the one or more flanges are contourable to match the host bone.

In one embodiment, the one or more flanges include a plurality of openings for receiving fasteners, locking or non-locking, for coupling the one or more flanges to the host bone.

The present disclosure also discloses a method for repairing an acetabular defect, the method includes inserting an acetabular cup into a target host bone; inserting a pre-assembled liner and flange construct within an interior cavity of the acetabular cup; securing one or more flanges of the pre-assembled liner and flange construct to host bone; and inserting a dual mobility bearing into an interior cavity of the pre-assembled liner and flange construct, the dual mobility bearing being arranged and configured to articulate relative to the pre-assembled liner and flange construct during use.

Embodiments of the present disclosure provide numerous advantages. For example, providing a dual mobility acetabular implant including a pre-assembled liner and flange construct facilitates incorporation of a larger femoral component as compared to conventional acetabular cup and cage systems. In addition, the pre-assembled liner and flange construct provides one or more flanges for coupling the implant to the host bone, which is in contrast with conventional dual mobility acetabular implants. That is, by directly coupling or associating one or more flanges in a pre-assembled liner and flange construct, elimination of a conventional cage is made possible, which thereby provides increased real estate to facilitate incorporation of a dual articulation bearing and resulting increased femoral head component, thereby reducing the risk of dislodgement.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, a specific embodiment of the disclosed device will now be described, with reference to the accompanying drawings, in which.

Figure 1:
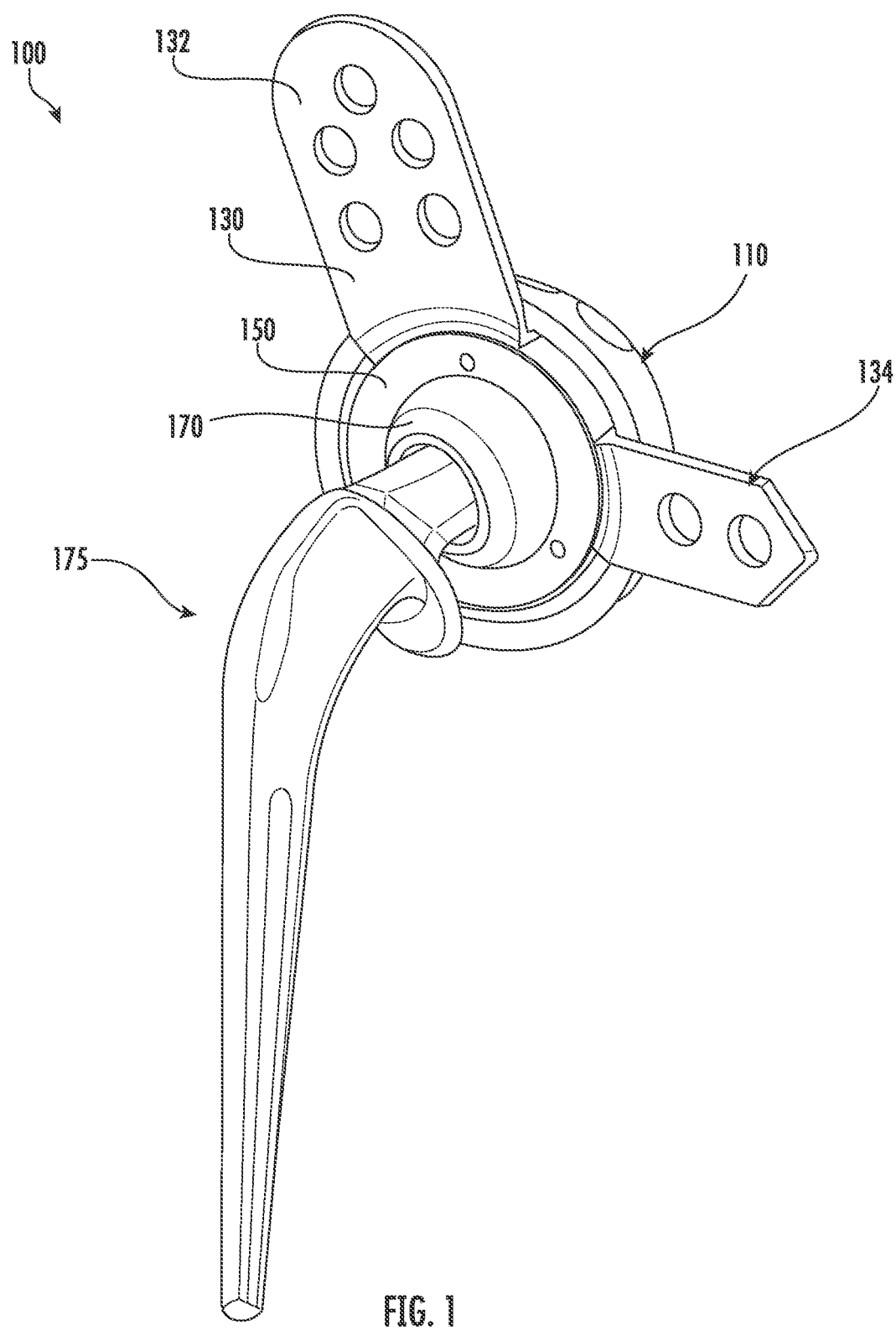
FIG. 1 shows a perspective view of a conventional acetabular implant (e.g., a convention cup-cage acetabular implant)
Figure 2:
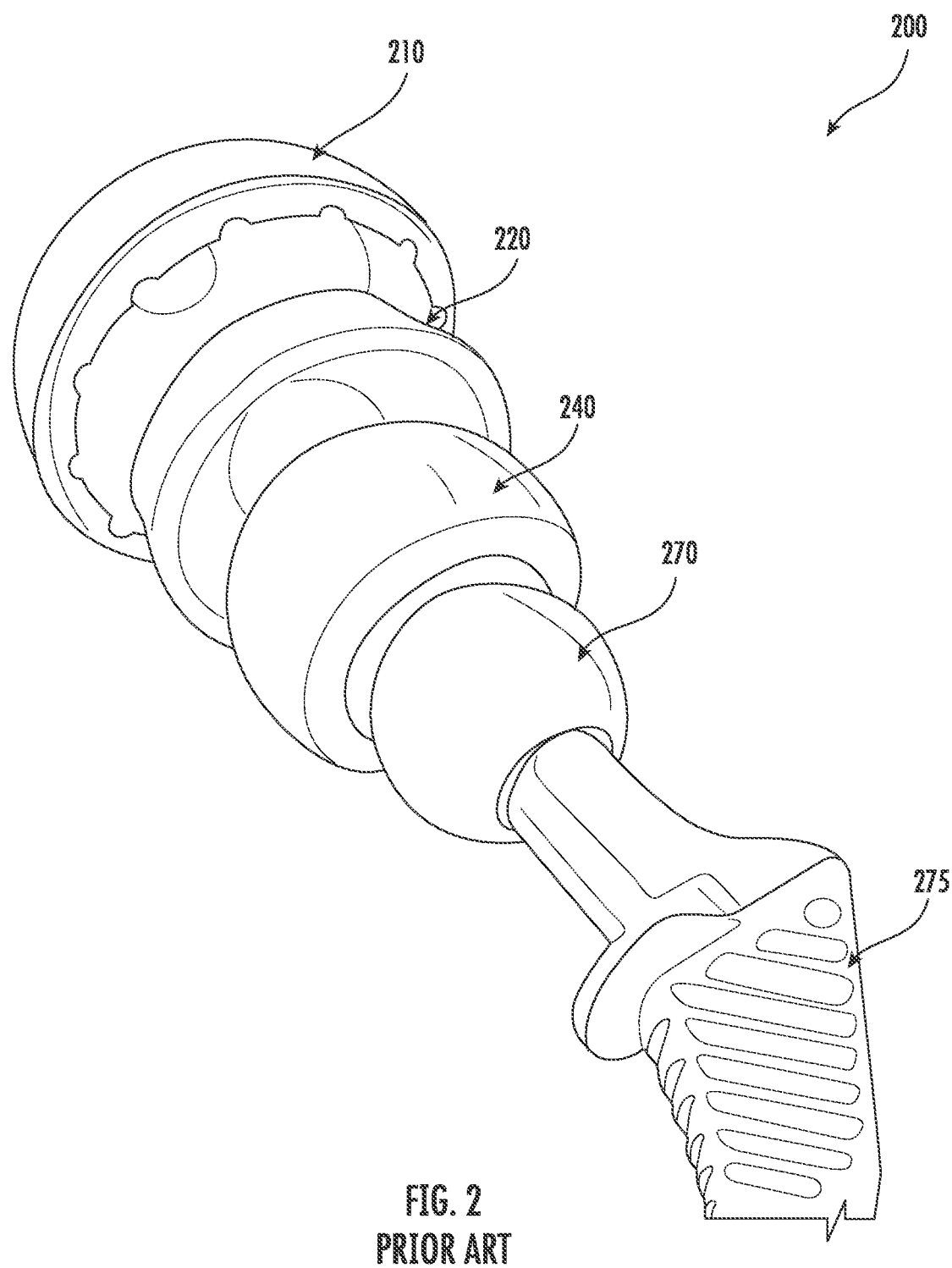
FIG. 2 shows an exploded, perspective view of a conventional dual mobility acetabular implant.

The drawings are not necessarily to scale. The drawings are merely representations, not intended to portray specific parameters of the disclosure. The drawings are intended to depict example embodiments of the disclosure, and therefore are not to be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

Embodiments of an improved dual mobility acetabular implant for hip revision surgery will now be described more fully hereinafter with reference to the accompanying drawings, in which preferred embodiments of the present disclosure are presented. As will be described and illustrated, in some embodiments, the improved dual mobility acetabular implant includes a pre-assembled liner and flange construct, system, device, etc. (used interchangeable herein without the intent to limit). Thus arranged, as will be described in greater detail, the dual mobility acetabular implant combines the dual articulating surfaces of conventional dual mobility acetabular implants with flanges of conventional cup-cage acetabular implants. In one embodiment, the dual mobility acetabular implant includes an acetabular cup, a pre-assembled liner and flange construct, and a dual mobility bearing (e.g., an insert and a femoral head).

Figure 3A:
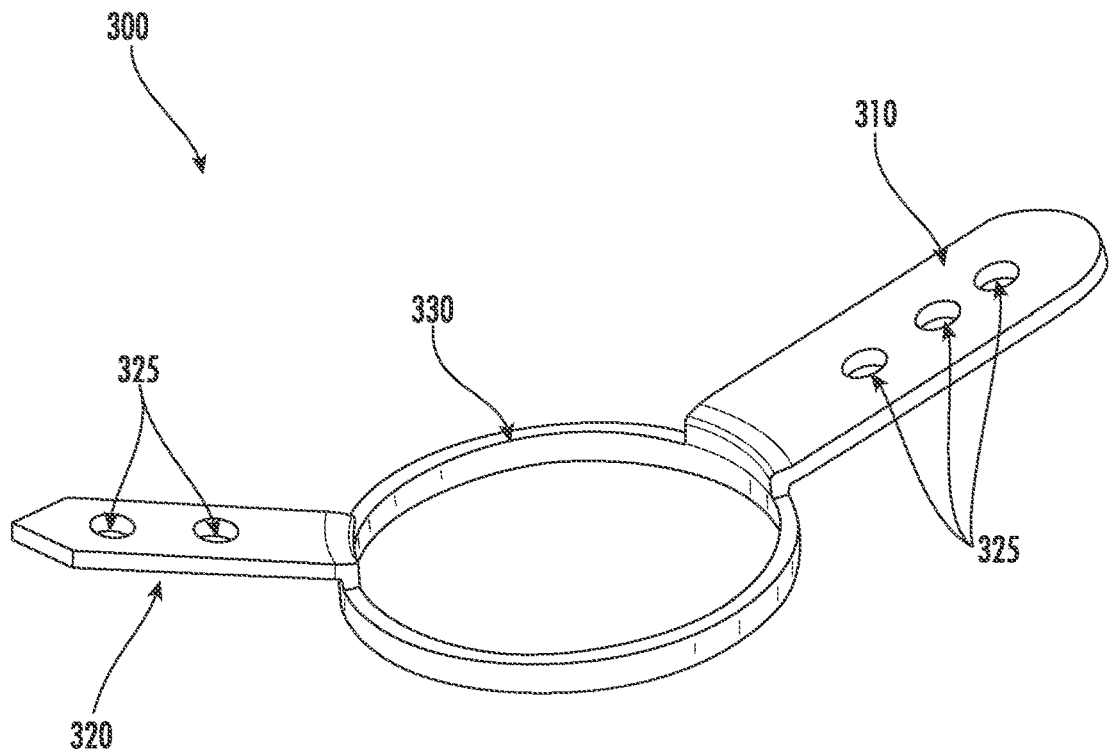
FIG. 3A shows a perspective view of an example of an embodiment of a flange device in accordance with aspects of the present disclosure, the flange device being arranged and configured to be operatively coupled with a liner for use in a dual mobility acetabular implant.
Figure 3B:
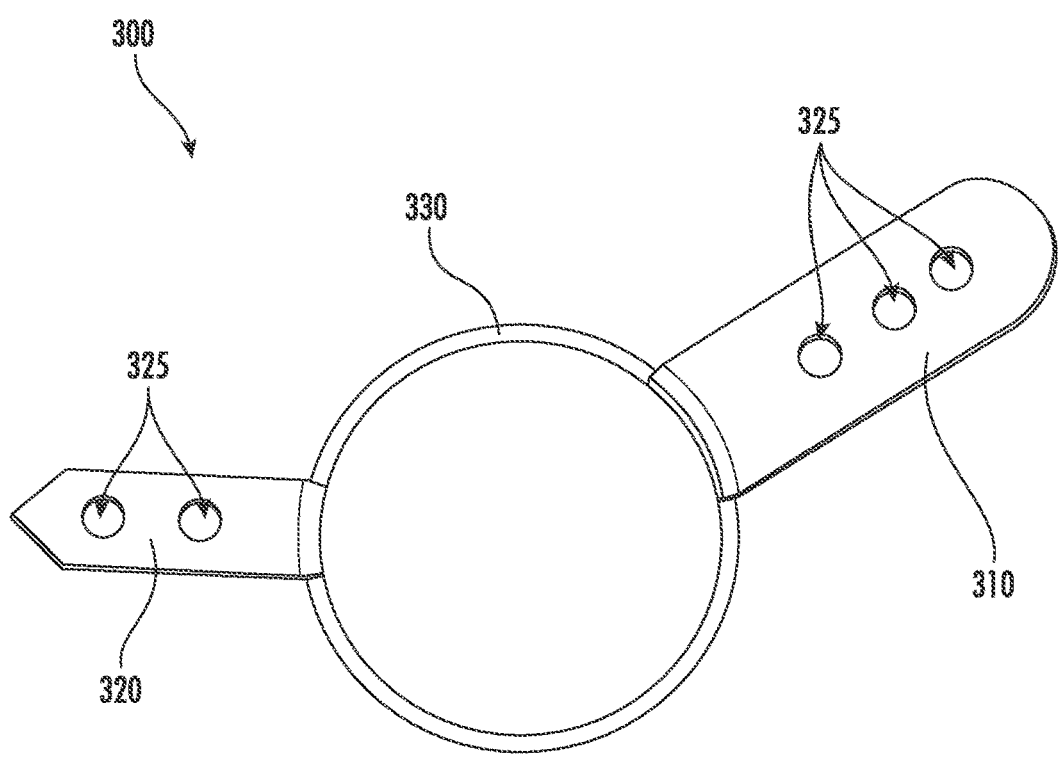
FIG. 3B shows a top view of the flange device shown in FIG. 3A.

Referring to FIGS. 3A and 3B a non-limiting example embodiment of a flange device or system 300 (used interchangeably herein without the intent to limit) that is arranged and configured to be used in combination with a liner in a dual mobility acetabular implant is illustrated. As shown, in one embodiment, the flange device 300 includes a first or superior flange 310 and a second or inferior flange 320, although the flange device 300 is not limited to a pair of flanges (e.g., first and second flanges 310, 320), and may include a greater or lesser number of flanges in other embodiments. For example, it is envisioned that the flange device 300 may include one, three, four, or more flanges.

Figure 3C:
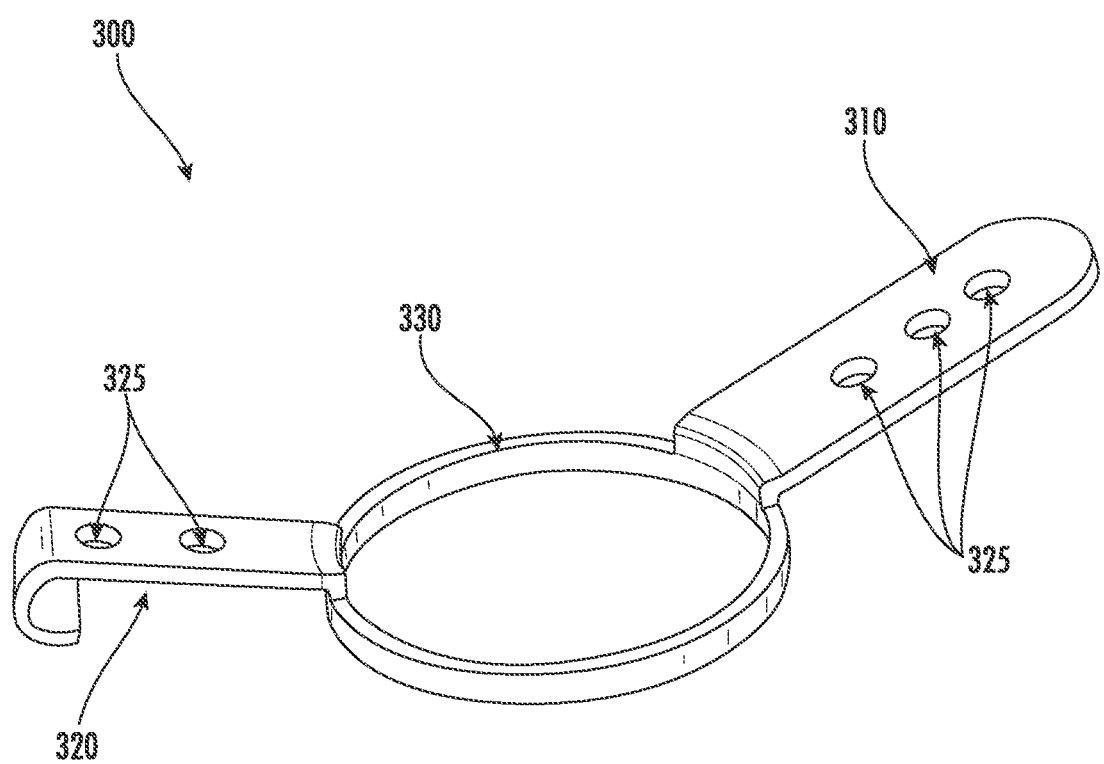
FIG. 3C shows a perspective view of an alternate embodiment of a flange device in accordance with aspects of the present disclosure, the flange device being substantially similar to the flange device of FIG. 3A, however, the inferior flange is arranged and configured with a hook or a hood.

As shown, each of the first and second flanges 310, 320 may include a plurality of openings 325 for receiving corresponding fasteners (not shown). In use, the fasteners extend through the openings 325 for engagement with host bone. The openings 325 may be any now known or hereafter developed openings for receiving fasteners and may be locking or non-locking screw holes. In use, the fasteners extend through the openings 325 for engagement with the patient's host bone. As will be appreciated by one of ordinary skill in the art, the number, size, position, and/or configuration of the openings 325 may be altered, and any number, size, position and/or configuration of openings 325 may be used. In addition, and/or alternatively, in some embodiments as depicted in FIG. 3C, the flanges such as, for example, the second or inferior flange 320 may be in the form of a hook or a hood for positioning between the patient's ischium and pubis. In addition, and/or alternatively, in some embodiments, the bone contacting surfaces of the first and second flanges 310, 320 may be solid or porous.

In use, the flanges 310, 320 may be operatively associated with, or coupled to, a liner for use in a dual mobility acetabular implant, as will be described in greater detail below. The flanges 310, 320 may be operatively associated with, or coupled to, the liner of a dual mobility acetabular implant by any now known or hereafter developed mechanism. For example, as shown in the non-limiting, illustrated example embodiment of FIGS. 3A and 3B, the flange device 300 may include a central body portion or band 330 from which the first and second flanges 310, 320 are coupled to and extend therefrom. As will be described in greater detail, the central body portion or band 330 is arranged and configured to engage the liner of a dual mobility acetabular implant. That is, for example, as will be illustrated, the band 330 can be arranged and configured to be pressed onto an outer, exterior surface of a liner.

As shown, the flange device 300 including the central band 330 and the first and second flanges 310, 320 may be integrally formed, although it is envisioned that they may also be separately formed and coupled together by any now known or hereafter developed mechanism such as, for example, via adhesives, fasteners, a mechanical or modular connection including, for example, locking grooves, tapers, or the like.

Figure 4A:
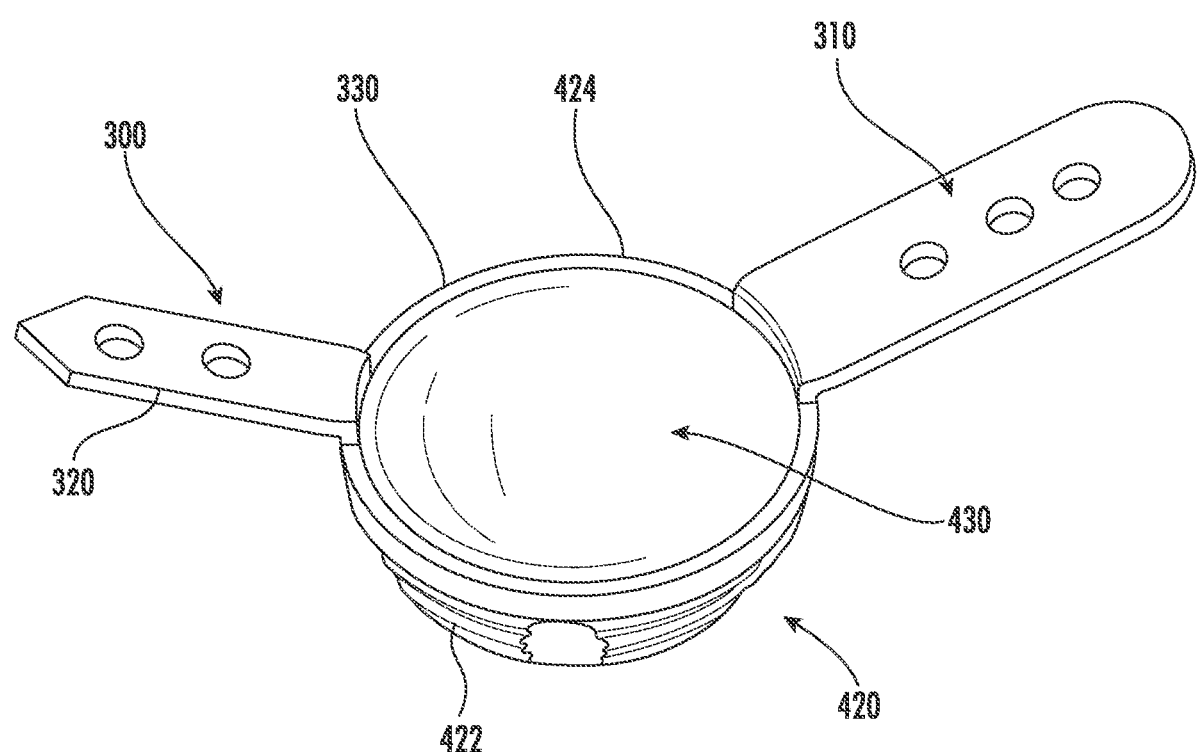
FIG. 4A shows a perspective view of the flange device shown in FIG. 3A pre-assembled to an example of an embodiment of a liner for use in a dual mobility acetabular implant in accordance with aspects of the present disclosure.
Figure 4B:
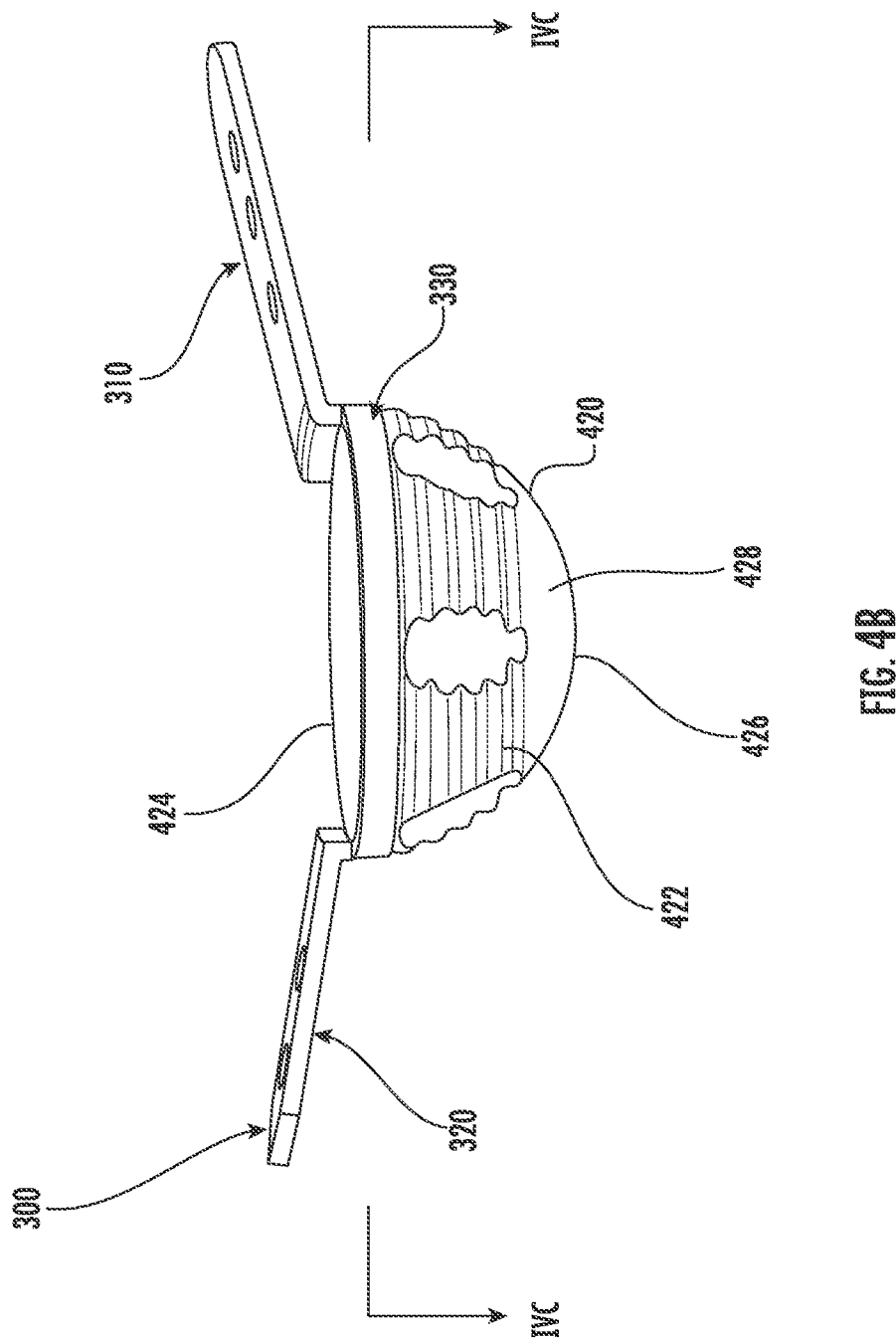
FIG. 4B shows a side, perspective view of the pre-assembled liner and flange construct shown in FIG. 4A.
Figure 4C:
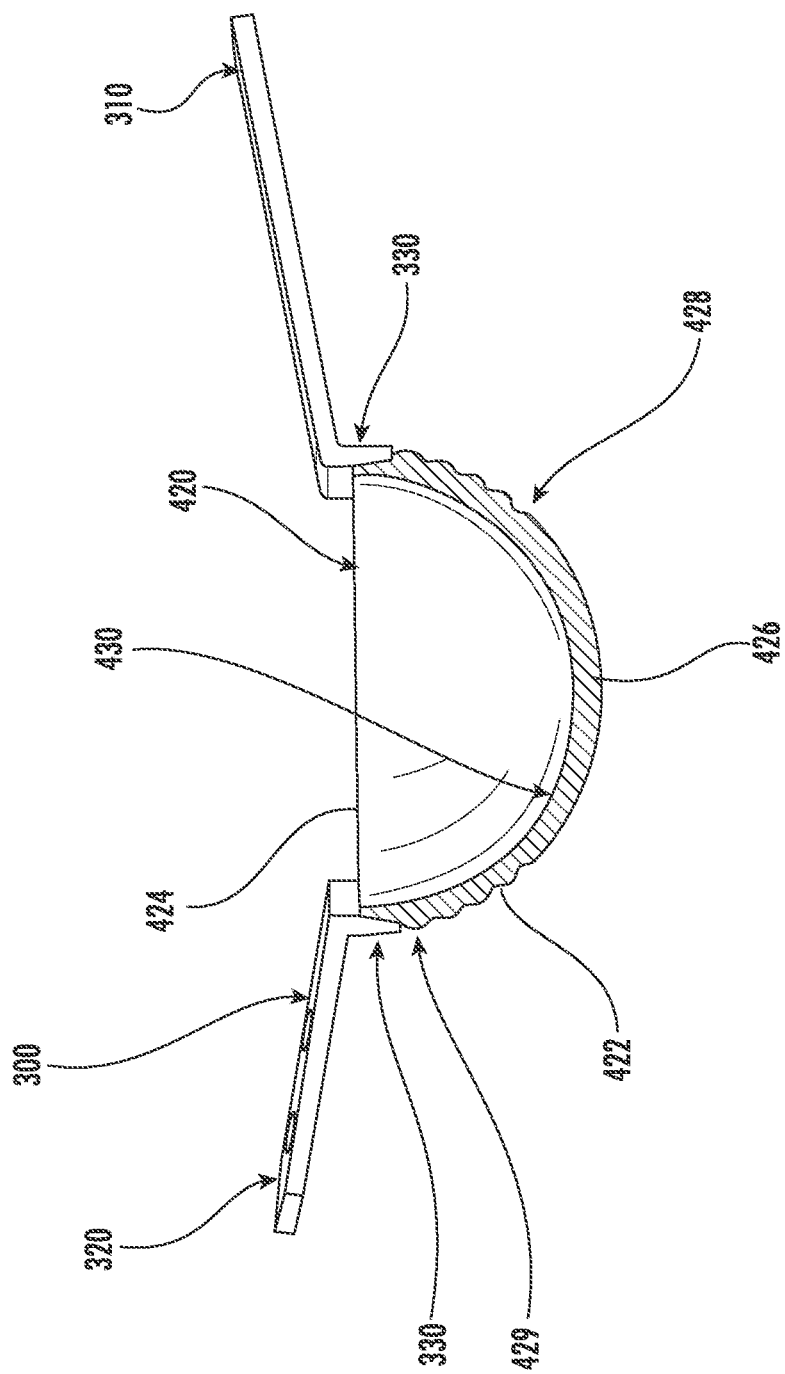
FIG. 4C shows a cross-sectional view of the pre-assembled liner and flange construct shown in FIG. 4A, taken alone line IVC-IVC in FIG. 4B.
Figure 5A:
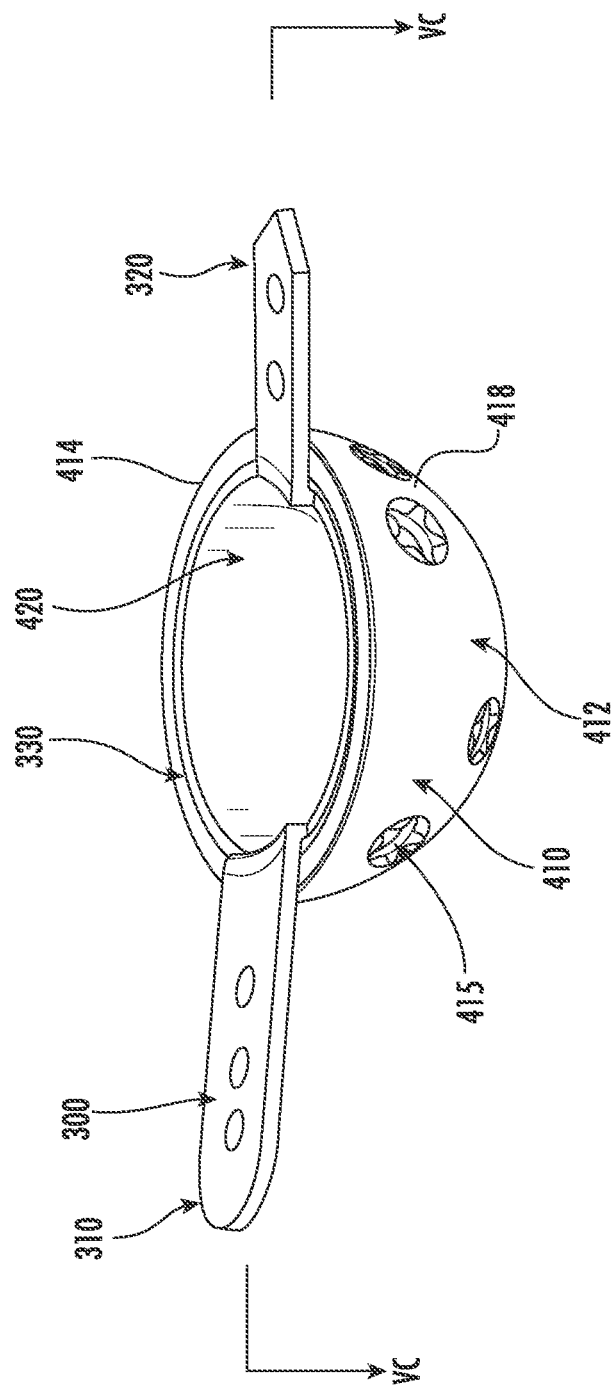
FIG. 5A shows a perspective view of the pre-assembled liner and flange construct shown in FIG. 4A positioned within an acetabular cup for use in a dual mobility acetabular implant in accordance with aspects of the present disclosure.
Figure 5B:
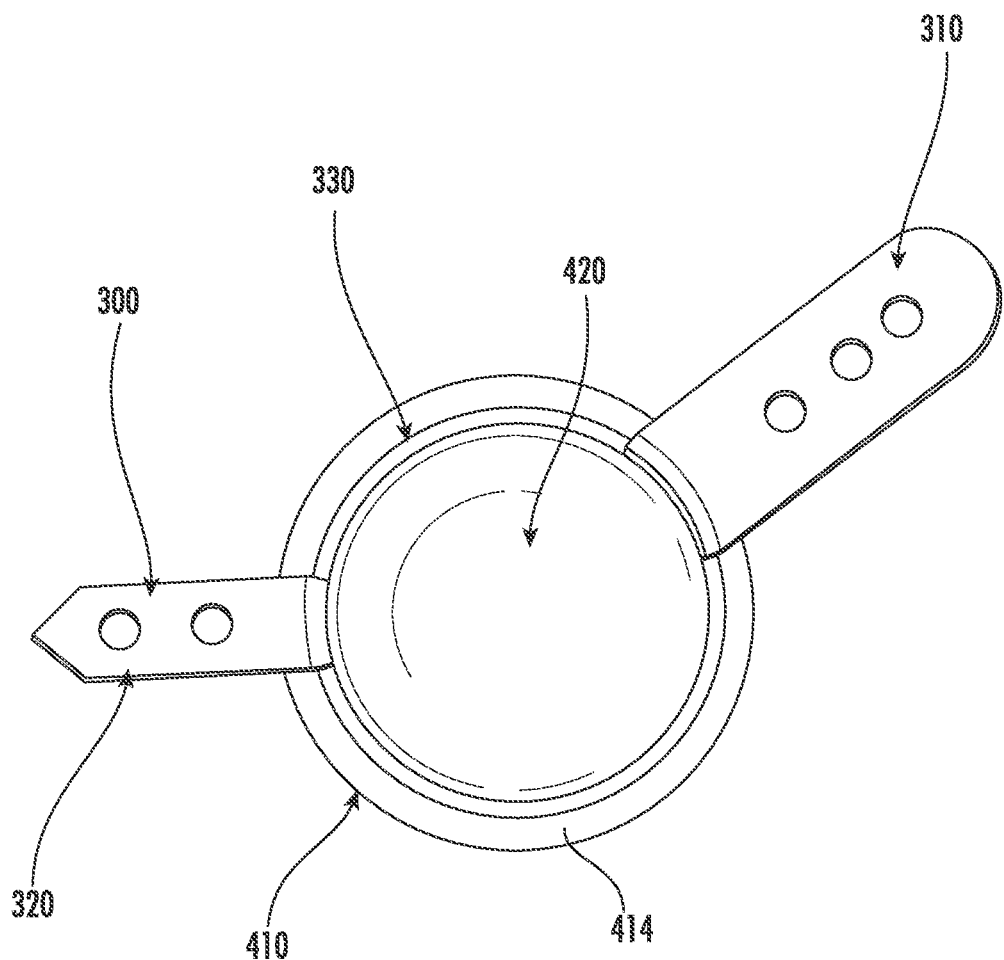
FIG. 5B shows a top view of the pre-assembled liner and flange construct positioned within the acetabular cup shown in FIG. 5A.

Referring to FIGS. 4A-4C, in one example embodiment, the flange device 300 may be coupled to a liner 420 of a dual mobility acetabular device. Thus arranged, the flange device 300 may be pre-assembled or initially coupled to the liner 420 to form a pre-assembled liner and flange construct. While the flange device 300 may be coupled to the liner 420 by any now known or hereafter developed mechanism, as shown, in one embodiment, the band 330 of the flange device 300 may be arranged and configured to be coupled to the liner 420. For example, as shown, the liner 420 may include a hollow body (hereinafter "body") 422 extending from an equatorial rim 424 to an apex or polar end 426 thereof. As shown, the body 422 may define a generally curved or convex exterior surface 428 and a generally curved or concave interior surface 430. In use, the equatorial rim 424 defines a circular opening for receiving an insert of a dual mobility acetabular device such as, for example, insert 240. That is, the liner 420 includes an interior cavity having a generally curved or concave interior surface 430 for contacting an outer curved surface of a dual articulating bearing (e.g., outer curved surface of an insert such as, for example, insert 240 so that the insert can articulate or move relative to the liner, and hence the pre-assembled liner and flange construct). The body 422 of the liner 420 is also arranged and configured to be inserted into contact with an acetabular cup of a dual mobility acetabular implant such as, for example, acetabular cup 210 or acetabular cup 410 (FIGS. 5A-5C), as will be described in greater detail below. Thus arranged, the pre-assembled liner and flange construct provides and/or combines an articulating surface for receiving the dual articulating bearing and one or more flanges for coupling to host bone.

As shown, in the illustrated embodiment, the exterior surface 428 of the liner 420 may include an outer surface or portion 429 located adjacent to the equatorial rim 424 for receiving, engaging, contacting, coupling, etc. the central band 330 of the flange device 300. In this manner, the flange device 300 may be coupled to the liner 420 by, for example, a taper-lock, a press-fit connection, etc., although it is envisioned that the flanges 310, 320 may be coupled to the liner 420 by any now known or hereafter developed mechanism including, for example, via mechanical fasteners, adhesives, etc. In one alternate embodiment, it is envisioned that the liner and the flanges may be monolithic or integrally formed as a single piece.

In this manner, the flanges 310, 320 can be pre-assembled to the liner 420 to form a pre-assembled liner and flange construct. Thereafter, referring to FIGS. 5A-5C, in one example of an embodiment, the pre-assembled liner and flange construct (e.g., liner 420 and flanges 310, 320) can be coupled, inserted, positioned within, etc. an acetabular cup 410 of a dual mobility acetabular implant such as, for example, acetabular cup 210. That is, as shown, the liner 420 may be arranged and configured to be coupled (e.g., received) within an interior portion or cavity of an acetabular cup 410, as would be readily appreciated by one of ordinary skill in the art. For example, as shown, the acetabular cup 410 may include a hollow body (hereinafter "body") 412 extending from an equatorial rim 414 to an apex or polar end 416 thereof. As shown, the body 412 may define a generally curved or convex exterior surface 418 and a generally curved or concave interior surface 419. In use, the equatorial rim 414 defines a circular opening for receiving the pre-assembled liner and flange construct. In use, the acetabular cup 410 is arranged and configured to be inserted into a patient's acetabulum. To this end, as shown, the acetabular cup 410 may include a plurality of openings 415 formed in the body 412, between the exterior surface 418 and the interior surface 419. In use, the plurality of openings 415 may receive a fastener (not shown) therein for securing the cup 410 to the patient's acetabulum. In use, the fasteners extend through the plurality of openings 415 for engagement with host bone (not shown). As will be appreciated by one of ordinary skill in the art, a greater or lesser number of openings 415 may be present in other embodiments. The openings 415 may take any configuration now known or hereafter developed, and may be locking or non-locking, and, further, locked openings may be fixed or polyaxial.

Thereafter, once the acetabular cup 410 has been coupled to the host bone, the pre-assembled liner and flange construct may be coupled to the acetabular cup 410. For example, the body 422 of the liner 420 may be positioned into the interior cavity of the cup 410. The liner 420 may be coupled to the acetabular cup 410 by any now known or hereafter developed mechanism including, for example, fasteners, cement, adhesive, etc.

Figure 5C:
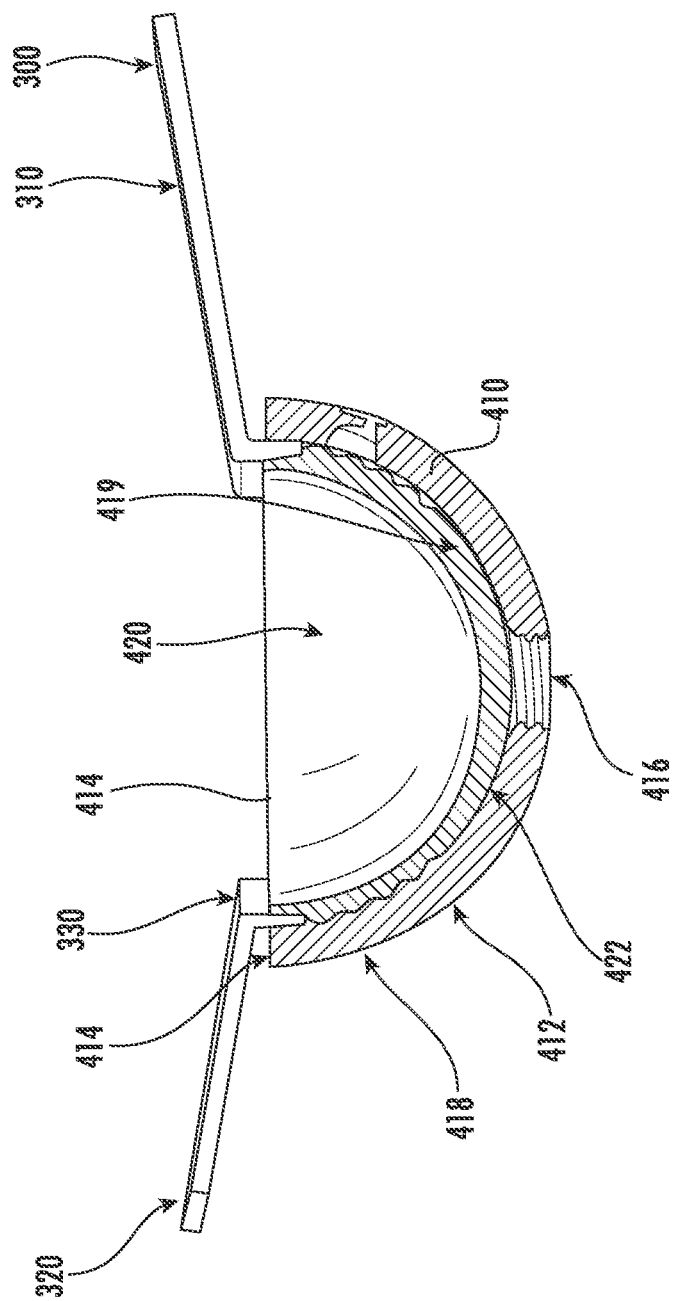
FIG. 5C shows a cross-sectional view of the pre-assembled liner and flange construct positioned within the acetabular cup shown in FIG. 5A, taken alone line VC-VC in FIG. 5A.

In one embodiment, as best illustrated in FIG. 5C, a gap or an equatorial clearance may be provided between the bottom or bone contacting surface of the flanges 310, 320 and the top face or rim 414 of the acetabular cup 410 to provide relief. In addition, and/or alternatively, a gap may be provided between the outer surface of the band 330 and the equatorial taper surface of the acetabular cup 410 to provide relief. In use, the relief(s) ensure that proper coupling between the liner 420 and the acetabular cup 410 (e.g., reliefs prevent the band 330 from interfering with the taper lock between the liner 420 and the acetabular cup 410).

In one embodiment, by providing a taper-lock or similar coupling between the flange device 300 and the liner 420, a surgeon can adjust the position of the flanges 310, 320 relative to the liner 420 intra-operatively. For example, the surgeon may elect to position the acetabular cup 410 into the patient's host bone to achieve optimal placement of the acetabular cup 410 relative to the bone. Next, the surgeon may elect to position the flanges 310, 320 to optimize placement of the flanges 310, 320 relative to the host bone. Subsequently, the surgeon may elect to position the liner 420 relative to the flange device 300 and acetabular cup 410. For example, in connection with a liner 420 utilizing a raised rim in a portion thereof to provide increased stability against dislocation in certain areas, the surgeon can adjust (e.g., rotate) the liner 420 relative to the flange device 300 and acetabular cup 410 to optimize location of the raised rim to provide increased stability against dislocation. As will be appreciated by one of ordinary skill in the art, a raised rim may be provided on a liner so that an area of the liner includes a rim that extends farther from the polar apex than another area of the liner to thereby restrict movement. In use, once all of the components are properly positioned, the surgeon may remove the components from the patient so that the final assembly including the flange device 300 and liner 420 can be impacted to secure relative positioning prior to final implantation.

In one example of an embodiment, a rotational center point of the liner 420 can be offset (e.g., lateralized, medialized, or eccentric) relative to a center point of the acetabular cup 410 in which it is received. Thus arranged, the rotational center point about which the bearing (e.g., insert 240 and femoral component 270) rotates can be adjusted.

In addition, and/or alternatively, in one example of an embodiment, the exterior surface 428 of the liner 420 may include a different angle, curvature, etc. relative to the interior surface 419 of the acetabular cup 410. Thus arranged, the liner 420 can be adjusted relative to the acetabular cup 410 (e.g., to adjust version—the tilt or angle of the face or the equatorial rim 424 of the liner 420 can be adjusted relative to the face or the equatorial rim 414 of the acetabular cup 410). That is, for example, in a revision total hip arthroplasty, where good host bone is absent or lacking, a surgeon may have to position the acetabular cup more retroverted and/or vertically such that it makes good contact with the host bone. By providing a liner that provides built-in anteversion, corrections can be made to achieve proper anatomical position (e.g., an anteverted liner reorients the opening relative to the acetabular cup).

In one example of an embodiment, in use, with the acetabular cup 410 positioned within a patient's acetabulum, the pre-assembled liner and flange construct may be initially positioned so that the liner 420 is positioned within the acetabular cup 410 (e.g., the body 422 of the liner 420 may be positioned into the interior cavity of the cup 410). Thereafter, the position of the pre-assembled liner and flange construct may be adjusted, moved, etc. relative to the position of the acetabular cup 410 (e.g., the position of the liner 420 may be moved relative to the acetabular cup 410). In doing so, the flanges 310, 320 will move along with the liner 420 since they are pre-assembled. Once the desired position of the pre-assembled liner and flange construct has been determined, the surgeon can manipulate, bend, etc. the flanges 310, 320 to better conform to the patient's bone. The first and second flanges 310, 320 of the pre-assembled liner and flange construct may be bent, manipulated, etc. by the surgeon in a manner that somewhat matches the patient's bone (e.g., patient's iliac and ischial anatomy).

The surgeon may then secure the liner 420 to the acetabular shell 410. For example, the exterior surface 428 of the liner 420 may be secured (e.g., adhered, cemented, etc.) to the interior surface 419 of the acetabular cup 410. Subsequently, the surgeon may fasten the pre-assembled liner and flange construct by, for example, inserting one or more fasteners through the plurality of openings 325 formed in the flanges 310, 320 for securing the pre-assembled liner and flange construct to the patient's bone thereby securing the position of the pre-assembled liner and flange construct. Fasteners may be inserted through the openings 325 formed in the flanges 310, 320 for securing the flanges 310, 320, and hence the acetabular implant, to host bone.

In connection with this example method of implantation, the liner 420 may be secured to the acetabular shell 410 before the flanges 310, 320 of the pre-assembled liner and flange construct are fastened to the patient's bone (e.g., ilium) to secure the pre-assembled liner and flange construct to the patient's bone. That is, in one example of a method of implantation, once the correct bend on the flanges are determined, the liner may be cemented into the acetabular cup prior to the flanges being coupled to the patient's bone. This provides advantages over conventional systems where a cage is assembled into a shell, and then a bearing is be cemented into the cage, although it is envisioned that the pre-assembled liner and flange construct can be used in methods where the flanges are coupled to the patient's bone prior to cementing the liner to the acetabular shell.

Next, a dual mobility bearing such as, for example, dual mobility bearing including insert 240 and femoral head component 270 may be received within, inserted, etc. the interior cavity of the liner 420.

Thus arranged, the example embodiment of the dual mobility acetabular implant may include flanges such as, for example, flanges 310, 320. In addition, the dual mobility acetabular implant may include a dual articulation bearing (e.g., insert 240 and femoral component 270). By this arrangement, a larger femoral component as compared to conventional acetabular cup and cage systems may be provided. In addition, the pre-assembled liner and flange construct provides one or more flanges for coupling the implant to the host bone, which is in contrast with conventional dual mobility acetabular implants. That is, by directly coupling or associating one or more flanges in a pre-assembled liner and flange construct, elimination of a conventional cage is made possible, which thereby provides increased real estate to facilitate incorporation of a dual articulation bearing and resulting increased femoral head component, thereby reducing the risk of dislodgement.

Although non-limiting, the acetabular cup may be made from many different materials including titanium, cobalt chrome, stainless steel, ceramic or other biocompatible material. In some embodiments, the exterior surface may be porous and may be comprised of titanium, cobalt chrome, polymer or other biocompatible material. In addition, the cup may be a combination of different biocompatible materials. For example, the cup may be cobalt chrome with a titanium porous coating on the exterior surface. Various manufacturing techniques may be used to manufacture the cup. For example, the cup be cast, additively manufactured, machined, or the like.

Similarly, although non-limiting, the flanges may be made from many different materials including titanium, cobalt chrome, stainless steel, ceramic or other biocompatible material. In some embodiments, the bone contacting surface of the flanges may be porous and may be comprised of titanium, cobalt chrome, polymer or other biocompatible material. In addition, the flanges may be a combination of different biocompatible materials. For example, the flanges may be cobalt chrome with a titanium porous coating on the exterior surface. Various manufacturing techniques may be used to manufacture the flanges. For example, the flanges may be cast, additively manufactured, machined, or the like.

Similarly, although non-limiting, the liner and/or the dual articulating bearing including, for example, the insert and the femoral head component, may be formed of any suitable material now known or hereafter developed including, for example, polyethylene material such as ultra-high molecular weight polyethylene, a ceramic material, or in some cases, even a metal such as, for example, cobalt chrome, stainless steel, titanium, etc. In one embodiment, the flanges may be manufactured from a metal. The liner may be manufactured from a ceramic or a metal, the metal can be ceramicised or non-ceramicised. In use, the bearing surfaces provide an articulating surface for the femoral head component to articulate relative to the insert and for the insert to articulate relative to the liner to track and accommodate the relative movement between the femur and the acetabulum.

In some embodiments, the liner and acetabular cup may include surface features adapted and configured to allow for improved cement adhesion between the liner and cup. The surface features may be provided in any suitable manner now known or hereafter developed including, for example, grooves, recesses, indentations, etc., formed along an exterior surface of the liner. The surface features may be oriented radially, spherically, or both. In various embodiments, the surface features may be arranged and configured to ensure a minimum distance between the liner and the cup for receiving cement.

In various non-limiting embodiments shown, the openings formed in the flanges and the acetabular cup may include fins or projections that extend radially inward from an inner surface of the openings and into an interior region thereof. The fins are configured to engage or cooperate with a head of a fastener (not shown) in order to secure the fastener at a desired position and at a desired angular orientation within the opening. In some embodiments, the openings may be provided with a relatively jagged or undulating inner circumference formed by the inwardly protruding fins, and concavities or indentations are formed between adjacent pairs of the fins which extend to a location adjacent the inner surface of the openings. Additionally, the inner surface may have a generally round configuration wherein the fins define convex protrusions extending inwardly into the openings. However, other shapes and configurations of the openings and/or the flexible fins are also contemplated.

In use, the flanges, the band, the liner, and the cup can have any suitable size, thickness, etc. For example, in some embodiments, the size of each flange may be based, for example, on the size of the acetabular cup. In various embodiments, the diameter of the band may have a 1:1 relationship with the diameter of the liner. The thickness of the band may be proportional to the diameter of the liner. Alternatively, the flange size and band thicknesses could be uniform.

Figure 6:
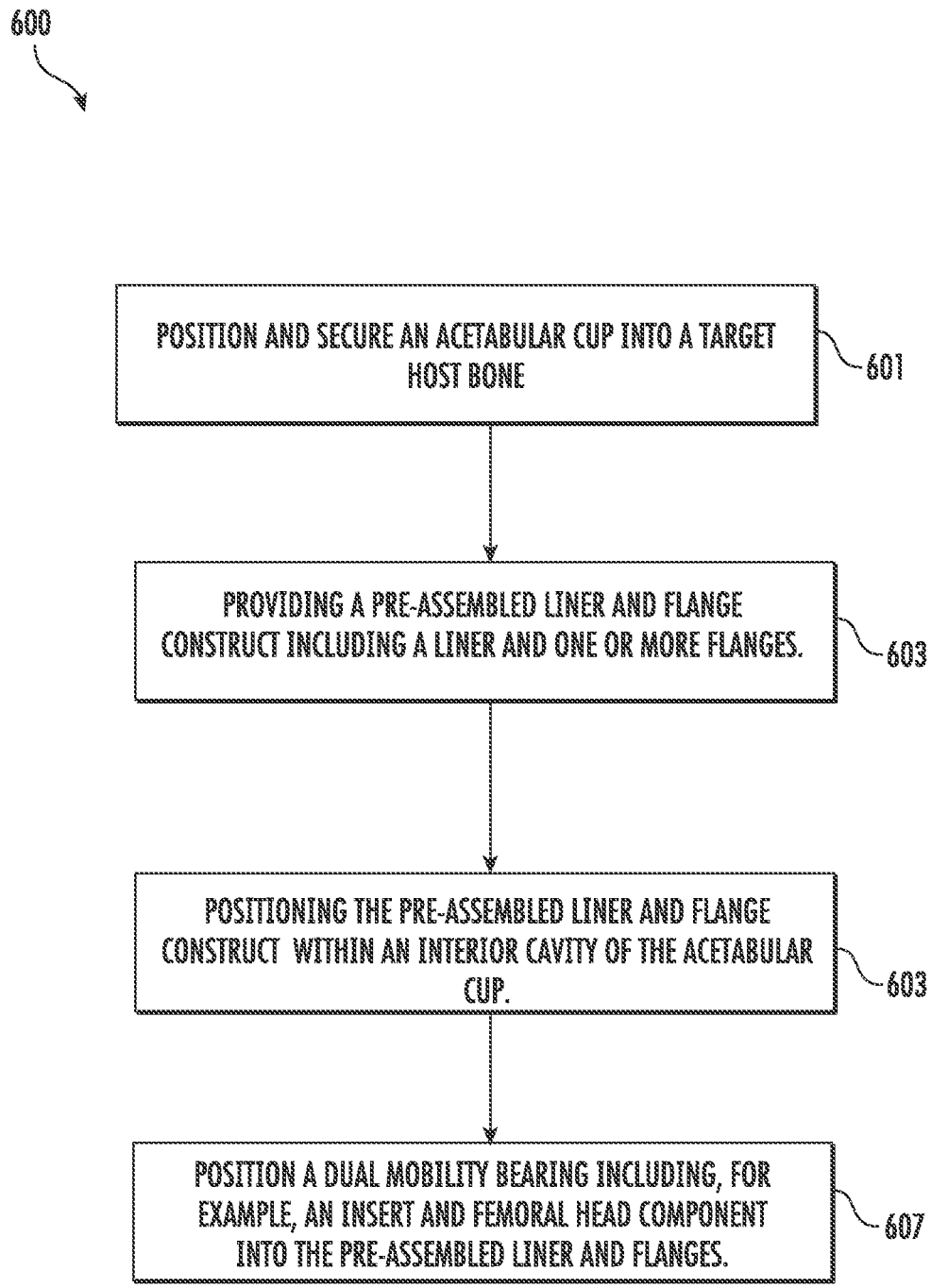
FIG. 6 depicts a method in accordance with embodiments of the disclosure.

Referring to FIG. 6, a non-limiting example embodiment of a method 600 is illustrated. In use, the acetabulum may be exposed and assessed identifying the location of quality bone. As needed, the acetabulum may be reconstructed using various instruments such as, impactors, reamers, etc. Next, at block 601, the method 600 may include positioning and securing an acetabular cup into a target host bone. The acetabular cup may be impacted into the target host bone and, in some embodiments, one or more optional fasteners may be inserted thru the cup and into the host bone. At block 603, the method 600 may include providing a pre-assembled liner and flange construct including a liner and one or more flanges associated therewith. At block 605, the method 600 may including positioning the pre-assembled liner and flange construct within an interior cavity of the acetabular cup. The method 600 may include securing the pre-assembled liner and flange construct to the cup. For example, in some embodiments, cement, adhesive, or the like may be used to secure the pre-assembled liner and flange construct to the cup. The flanges may then be secured to host bone. The flanges of the pre-assembled liner and flange construct may be properly positioned and, in some embodiments, the flanges may be properly contoured as needed. The flanges may include a plurality of openings for receiving corresponding fasteners. In use, the fasteners extend through the openings for engagement with host bone.

Alternatively, after the pre-assembled liner and flange construct has been properly positioned relative to the cup, cement may be inserted, injected, or the like into the liner to, inter alia, facilitate better coupling between the liner and the cup. Alternatively, it should be appreciated that the cement may be inserted, injected, or the like prior to insertion of the liner into the cup. It should be appreciated that the cement may be inserted, injected, or the like into the cup before, after, or both in relation to timing of liner placement. Finally, at block 607, the method 600 may include positioning a dual mobility bearing including, for example, an insert and femoral head component into the pre-assembled liner and flange construct.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure.

Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. A dual mobility acetabular implant arranged and configured to be implanted into a patient's acetabulum, the dual mobility acetabular implant comprising:
   an acetabular cup having a curved outer surface arranged and configured to contact a patient's acetabulum and an interior cavity having an interior curved surface;
   a pre-assembled liner and flange construct, the pre-assembled liner and flange construct being arranged and configured to be at least partially received within the interior cavity of the acetabular cup, the pre-assembled liner and flange construct including:
      a liner having a curved outer surface arranged and configured to contact the interior curved surface of the acetabular cup and an interior cavity having an interior curved surface, the curved outer surface including an exterior surface portion having a tapered profile; and
      a flange device including a body portion engaging the tapered profile of the exterior surface of the liner and one or more flanges extending from the body portion, the one or more flanges arranged and configured to contact host bone; and
   a dual articulating bearing including an insert and a femoral component, the insert having a curved outer surface arranged and configured to contact and articulate relative to the interior curved surface of the liner and an interior curved surface arranged and configured to contact and articulate relative to an outer curved surface of the femoral head component.

2. The dual mobility acetabular implant of claim 1, wherein the body portion of the flange device is arranged and configured to be press-fitted onto the curved outer surface of the liner.

3. The dual mobility acetabular implant of claim 1, wherein the pre-assembled liner and flange construct including the liner and the flange device is integrally formed.

4. The dual mobility acetabular implant of claim 1, wherein the pre-assembled liner and flange construct is coupled to the acetabular cup so that relative movement therebetween is inhibited.

5. The dual mobility acetabular implant of claim 1, wherein a rotational center point of the liner is offset relative to a center point of the acetabular cup.

6. The dual mobility acetabular implant of claim 1, wherein an exterior surface of the liner includes a different angle, a different curvature, or a combination thereof, relative to an interior surface of the acetabular cup so that the liner is movable relative to the acetabular cup.

7. The dual mobility acetabular implant of claim 1, wherein the flange device is integrally formed.

8. The dual mobility acetabular implant of claim 1, wherein the acetabular cup includes one or more openings arranged and configured to receive one or more fasteners, respectively, for coupling the acetabular cup to the patient's acetabulum.

9. The dual mobility acetabular implant of claim 1, wherein the one or more flanges are contourable to match the host bone.

10. The dual mobility acetabular implant of claim 1, wherein the one or more flanges include a plurality of openings for receiving fasteners for coupling the one or more flanges to the host bone.

11. A dual mobility acetabular implant arranged and configured to be implanted into a patient's acetabulum, the dual mobility acetabular implant comprising:
    an acetabular cup having a curved outer surface arranged and configured to contact a patient's acetabulum and an interior cavity having an interior curved surface;
    a pre-assembled liner and flange construct at least partially received within the interior cavity of the acetabular cup, the pre-assembled liner and flange construct including:
        a liner having a curved outer surface contacting the interior curved surface of the acetabular cup and an interior cavity having an interior curved surface, the curved outer surface including an exterior surface portion having a tapered profile; and
        a flange device including a body portion arranged and configured to engage the tapered profile of the exterior surface of the liner and one or more flanges extending from the body portion, the one or more flanges arranged and configured to contact host bone; and
    a dual articulating bearing including an insert and a femoral component, the insert having a curved outer surface to contact and articulate relative to the interior curved surface of the liner and an interior curved surface to contact and articulate relative to an outer curved surface of the femoral head component.

12. The dual mobility acetabular implant of claim 11, wherein the body portion of the flange device is press-fitted onto the curved outer surface of the liner.

13. The dual mobility acetabular implant of claim 11, wherein the pre-assembled liner and flange construct including the liner and the flange device is integrally formed.

14. The dual mobility acetabular implant of claim 11, wherein the pre-assembled liner and flange construct is coupled to the acetabular cup so that relative movement therebetween is inhibited.

15. The dual mobility acetabular implant of claim 11, wherein a rotational center point of the liner is offset relative to a center point of the acetabular cup.

16. The dual mobility acetabular implant of claim 11, wherein an exterior surface of the liner includes a different angle, a different curvature, or a combination thereof, relative to an interior surface of the acetabular cup so that the liner is movable relative to the acetabular cup.

17. The dual mobility acetabular implant of claim 11, wherein the flange device is integrally formed.

18. The dual mobility acetabular implant of claim 11, wherein the acetabular cup includes one or more openings arranged and configured to receive one or more fasteners, respectively, for coupling the acetabular cup to the patient's acetabulum.

19. The dual mobility acetabular implant of claim 11, wherein the one or more flanges are contourable to match the host bone.

20. The dual mobility acetabular implant of claim 11, wherein the one or more flanges include a plurality of openings for receiving fasteners for coupling the one or more flanges to the host bone.

* * * * *